(12) United States Patent
Merla et al.

(10) Patent No.: US 7,842,812 B2
(45) Date of Patent: Nov. 30, 2010

(54) SUBSTITUTED 5-AMINOMETHY1-1H-PYRROLE-2-CARBOXYLIC ACID AMIDES

(75) Inventors: Beatrix Merla, Aachen (DE); Corinna Sundermann, Aachen (DE); Utz-Peter Jagusch, Aachen (DE); Werner Englberger, Stolberg (DE); Hagen-Heinrich Hennies, Simmerath (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/600,827

(22) Filed: Nov. 17, 2006

(65) Prior Publication Data

US 2007/0135494 A1 Jun. 14, 2007

Related U.S. Application Data

(63) Continuation of application No. PCT/EP2005/005403, filed on May 17, 2005.

(30) Foreign Application Priority Data

May 17, 2004 (DE) .................... 10 2004 024 772

(51) Int. Cl.
C07D 211/06 (2006.01)
A61K 31/454 (2006.01)

(52) U.S. Cl. ..................... 546/193; 514/326

(58) Field of Classification Search .......... 546/193; 514/326
See application file for complete search history.

(56) References Cited

U.S. PATENT DOCUMENTS

2005/0288342 A1 12/2005 Merla et al.

FOREIGN PATENT DOCUMENTS

DE 102 61 131 A1 7/2004

WO WO 99/12933 A2 3/1999
WO WO 03/035649 A1 5/2003

OTHER PUBLICATIONS

Kubinyi (3D QSAR in Drug Design: Ligand-Protein Interactions and Molecular Similarity, vol. 2-3, Springer, 1998, 800 pages.) TOC and pp. 243-244 provided.*
Byrn et al., Pharm. Res., v. 12, n. 7, p. 945-54, 1995.*
Page' et al., Bioorg. Med. Chem. Lett. 13 (2003) 1585-1589.*
Zaveri et al., European Journal of Pharmacology 428, (2001), 29-36.*
Subramanian et al., J. Med. Chem. (2000), 43, 381-391.*
Harry Heaney, et al., The Generation of Iminium Ions Using Chlorosilanes and Their Reactions with Electron Rich Aromatic Heterocycles, Tetrahedron, 1997, pp. 2941-2958, vol. 53, No. 8, Elsevier Science Ltd., Great Britain.
English translation of International Preliminary Report on Patentability dated Feb. 8, 2007 (six (6) pages).
M.K. Scott et al.: "Piperazinylalkyl Heterocycles as Potential Antipsychotic Agents" Journal of Medical Chemistry, vol. 38, pp. 4198-4210, XP002349085, American Chemical Society, Washington.
International Search Report dated Oct. 24, 2005 (Three (3) pages).
German Search Report dated Mar. 7, 2005 with English translation thereof (Eight (8) pages).

* cited by examiner

Primary Examiner—Robert Havlin
(74) Attorney, Agent, or Firm—Crowell & Moring LLP

(57) ABSTRACT

Substituted 5-aminomethyl-1H-pyrrole-2-carboxylic acid amides, a process for the production thereof, pharmaceutical preparations containing these compounds and the use of these compounds in pharmaceutical preparations for treatment or inhibition of withdrawal symptoms, memory disorders, neurodegenerative diseases, epilepsy, cardiovascular disorders, water retention, intestinal motility disorders, urinary incontinence, anorexia, tinnitus, pruritus, depression, sexual dysfunction, airways diseases, food intake disorders, or type II (non-insulin-dependent) diabetes, or for anxiolysis, diuresis, suppression of the urinary reflex, reducing the addictive potential of opioids, modulating locomotor activity, influencing the cardiovascular system, or regulating electrolyte balance.

17 Claims, No Drawings

SUBSTITUTED 5-AMINOMETHYl-1H-PYRROLE-2-CARBOXYLIC ACID AMIDES

CROSS REFERENCE TO RELATED APPLICATIONS

This application is a continuation of international patent application no. PCT/EP2005/005403, filed May 17, 2005, designating the United States of America and published in German on Dec. 1, 2005 as WO 2005/113497, the entire disclosure of which is incorporated herein by reference. Priority is claimed based on Federal Republic of Germany patent application no DE 10 2004 024 772.2, filed May 17, 2004.

BACKGROUND OF THE INVENTION

The present invention relates to substituted 5-aminomethyl-1H-pyrrole-2-carboxylic acid amide compounds, to a process for the production thereof, to pharmaceutical preparations containing these compounds and to the use of these compounds in the treatment and/or inhibition of various disease states or disorders.

Pain is a basic clinical symptom. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain, but they exhibit unwanted accompanying symptoms, such as for example respiratory depression, vomiting, sedation or constipation. Research is being carried out worldwide into other pain-relieving agents.

SUMMARY OF THE INVENTION

The object of the present invention was accordingly to provide novel active ingredients which are in particular suitable as pharmacological active ingredients for use in pharmaceutical preparations, preferably in pharmaceutical preparations for treating pain.

This object has been achieved by the provision of the substituted 5-aminomethyl-1H-pyrrole-2-carboxylic acid amides according to the invention of formula I below.

It has surprisingly been found that the substituted 5-aminomethyl-1H-pyrrole-2-carboxylic acid amides according to the invention of formula I below exhibit elevated affinity for the opioid receptors, in particular for μ opioid receptors, and are accordingly suitable for regulating these receptors.

The substituted 5-aminomethyl-1H-pyrrole-2-carboxylic acid amides according to the invention of formula I below are furthermore suitable for regulating, preferably for inhibiting, noradrenaline (NA) uptake and for regulating, preferably for inhibiting, 5-hydroxytryptamine (5-HT) uptake.

The substituted 5-aminomethyl-1H-pyrrole-2-carboxylic acid amides according to the invention of formula I below may accordingly in particular be used as pharmacological active ingredients in pharmaceutical preparations for the prevention and/or treatment of disorders or diseases associated with the above-stated receptors or processes.

The present invention accordingly provides substituted 5-aminomethyl-1H-pyrrole-2-carboxylic acid amides of formula I,

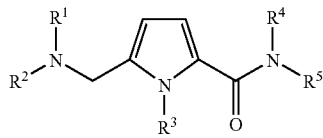

in which $R^1$ and $R^2$, together with the nitrogen atom joining them together as a ring member, form a saturated or unsaturated, unsubstituted or at least monosubstituted cycloaliphatic residue optionally comprising at least one further heteroatom as a ring member;

$R^3$ denotes a linear or branched, saturated or unsaturated, unsubstituted or at least monosubstituted aliphatic residue, a saturated or unsaturated, unsubstituted or at least monosubstituted cycloaliphatic residue optionally comprising at least one heteroatom as a ring member, which cycloaliphatic residue may be attached via a linear or branched alkylene group, or denotes an unsubstituted or at least monosubstituted aryl or heteroaryl residue, which may be attached via a linear or branched alkylene group;

$R^4$ denotes a hydrogen residue, a linear or branched, saturated or unsaturated, unsubstituted aliphatic residue, a saturated or unsaturated, unsubstituted or at least monosubstituted cycloaliphatic residue optionally comprising at least one heteroatom as a ring member, which cycloaliphatic residue may be attached via a linear or branched alkylene group, or denotes an unsubstituted or at least monosubstituted aryl or heteroaryl residue attached via a linear or branched alkylene group;

$R^5$ denotes a linear or branched, saturated or unsaturated, unsubstituted aliphatic residue, a saturated or unsaturated, unsubstituted or at least monosubstituted cycloaliphatic residue optionally comprising at least one heteroatom as a ring member, which cycloaliphatic residue may be attached via a linear or branched alkylene group, or denotes an unsubstituted or at least monosubstituted aryl or heteroaryl residue attached via a linear or branched alkylene group; or $R^4$ and $R^5$, together with the nitrogen atom joining them together as a ring member, form a saturated or unsaturated, unsubstituted or at least monosubstituted cycloaliphatic residue optionally comprising at least one further heteroatom as a ring member, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

Compounds of formula I, in which:

$R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue, $R^4$ denotes a hydrogen residue; and $R^5$ denotes an iso-propyl residue, in the form of the fumarate salt, $R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue, $R^4$ denotes a hydrogen residue and $R^5$ denotes a methyl residue, in the form of the fumarate salt, $R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue and $R^4$ and $R^5$, together with the nitrogen atom joining them together, form a piperidinyl residue, in the form of the hydrates of the hydrochloride salt, and $R^1$ and $R^2$, together with the nitrogen atom joining them together as a ring member, form a piperazinyl residue, which is substituted on the other nitrogen atom in position 4 with an o-(methoxy)-phenyl residue, $R^3$ denotes a methyl residue, $R^4$ denotes a hydrogen residue; and $R^5$ denotes a methyl residue, in the form of the fumarate salt, are preferably excepted.

Compounds of formula I, in which:

$R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue, $R^4$ denotes a hydrogen residue; and $R^5$ denotes an iso-propyl residue, $R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue, $R^4$ denotes a hydrogen residue and $R^5$ denotes a methyl residue, $R^1$ and $R^2$, together with the nitrogen atom joining them together as a ring member, form a piperazinyl residue, which is substituted on the other nitrogen atom in position 4 with an o-(iso-propyloxy)-phenyl residue, $R^3$ denotes a methyl residue and $R^4$ and $R^5$, together with the nitrogen atom joining them together, form a piperidinyl residue, $R^1$ and $R^2$, together with the nitrogen atom joining them together as a ring member, form a piperazinyl residue, which is substituted on the other nitrogen atom in position 4 with an o-(methoxy)-phenyl residue, $R^3$ denotes a methyl residue, $R^4$ denotes a hydrogen residue and $R^5$ denotes a methyl residue, and the respective corresponding salts and/or hydrates thereof are particularly preferably excepted.

Preferred substituted 5-aminomethyl-1H-pyrrole-2-carboxylic acid amides according to the invention of formula I are those in which the residues $R^1$ and $R^2$ together with the nitrogen atom to which they are attached form a saturated or unsaturated, unsubstituted or at least monosubstituted 4-, 5-, 6-, 7-, 8- or 9-membered cycloaliphatic residue optionally comprising at least one further heteroatom as a ring member, and the respective residues $R^3$ to $R^5$ have the above-stated meanings.

Preferably $R^1$ and $R^2$ together with the nitrogen atom to which they are attached form a saturated or unsaturated 4-, 5-, 6-, 7-, 8- or 9-membered cycloaliphatic residue optionally comprising at least one further heteroatom selected from the group consisting of nitrogen, oxygen and sulfur as a ring member, which cycloaliphatic residue may be identically or differently mono- or polysubstituted with a substituent selected from the group consisting of $C_{1-5}$ alkyl, —C(═O)—O—$C_{1-5}$-alkyl, —O—$C_{1-5}$-alkyl, Cl, F, Br, I, —C(═O)—NH$_2$, —C(═O)—NH—$C_{1-5}$-alkyl, —C(═O)—N($C_{1-5}$-alkyl)$_2$, —C(═O)—$C_{1-5}$-alkyl, —NH$_2$, —NH—$C_{1-5}$-alkyl, —N($C_{1-5}$-alkyl)$_2$, furanyl thiophenyl, pyridinyl, phenyl and benzyl, wherein the cyclic substituents may themselves be unsubstituted or at least monosubstituted.

Particularly preferably $R^1$ and $R^2$ together with the nitrogen atom to which they are attached form an imidazolidinyl, aziridinyl, azetidinyl, pyrrolidinyl, piperidinyl, azepanyl, azocanyl, piperazinyl, morpholinyl or thiomorpholinyl residue, which residue may be identically or differently mono- or polysubstituted with a substituent selected from the group consisting of $C_{1-5}$ alkyl, —C(═O)—O—$C_{1-5}$-alkyl, O—$C_{1-5}$-alkyl, Cl, F, Br, I, —C(═O)—NH$_2$, —C(═O)—NH—$C_{1-5}$-alkyl, —C(═O)—N($C_{1-5}$-alkyl)$_2$, —C(═O)—$C_{1-5}$-alkyl, —NH$_2$, —NH—$C_{1-5}$-alkyl, —N($C_{1-5}$-alkyl)$_2$, furanyl, thiophenyl, pyridinyl, phenyl and benzyl, wherein the cyclic substituents may themselves be unsubstituted or at least monosubstituted.

The compounds of the invention advantageously may be present in the form of the pure stereoisomers thereof, in particular enantiomers or diastereomers, the racemates thereof or in the form of mixtures of the stereoisomers, in particular the enantiomers, diastereomers and/or rotamers thereof, in any desired mixing ratio, and/or in the form of the respective corresponding salts and/or solvates thereof.

Further preferred substituted 5-aminomethyl-1H-pyrrole-2-carboxylic acid amides according to the invention of formula I are those in which residue $R^3$ denotes a linear or branched, saturated or unsaturated, unsubstituted or at least monosubstituted aliphatic $C_{1-10}$ residue, a saturated or unsaturated, unsubstituted or at least monosubstituted 3-, 4-, 5-, 6-, 7-, 8- or 9-membered cycloaliphatic residue optionally comprising at least one heteroatom as a ring member, which cycloaliphatic residue may be attached via a linear or branched $C_{1-3}$ alkylene group, or denotes an unsubstituted or at least monosubstituted 5- to 14-membered aryl or heteroaryl residue, which may be attached via a linear or branched $C_{1-3}$ alkylene group.

$R^3$ preferably denotes a linear or branched, unsubstituted or at least monosubstituted $C_{1-5}$ alkyl residue, a saturated or unsaturated, unsubstituted or at least monosubstituted 4-, 5-, 6-, 7-, 8- or 9-membered cycloaliphatic residue, which may be attached via a linear or branched $C_{1-3}$ alkylene group or denotes an unsubstituted or at least monosubstituted 5- or 6-membered aryl or heteroaryl residue, which may be attached via a linear or branched $C_{1-3}$ alkylene group.

$R^3$ particularly preferably denotes an alkyl residue selected from the group consisting of methyl, ethyl, n-propyl, iso-propyl, n-butyl, iso-butyl, sec-butyl and tert-butyl, and in each case the residues $R^1$, $R^2$, $R^4$ and $R^5$ have the above-stated meaning, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

Substituted 5-aminomethyl-1H-pyrrole-2-carboxylic acid amides according to the invention of formula I which are furthermore preferred are those in which $R^4$ denotes a hydrogen residue, a linear or branched, saturated or unsaturated, unsubstituted aliphatic $C_{1-10}$ residue, a saturated or unsaturated, unsubstituted or at least monosubstituted 3-, 4-, 5-, 6-, 7-, 8- or 9-membered cycloaliphatic residue optionally comprising at least one heteroatom as a ring member, which cycloaliphatic residue may be attached via a linear or branched $C_{1-3}$ alkylene group, or denotes an unsubstituted or at least monosubstituted 5- to 14-membered aryl or heteroaryl residue attached via a linear or branched $C_{1-3}$ alkylene group.

$R^4$ preferably denotes a hydrogen residue, a linear or branched, unsubstituted $C_{1-5}$ alkyl residue, an unsaturated or saturated, unsubstituted or at least monosubstituted 3-, 4-, 5-, 6-, 7-, 8- or 9-membered cycloaliphatic residue, or denotes an unsubstituted or at least monosubstituted phenyl residue attached via a linear or branched $C_{1-3}$ alkylene group.

$R^4$ particularly preferably denotes a hydrogen residue, an alkyl residue selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl residue or denotes an unsubstituted or at least monosubstituted benzyl residue and in each case the residues $R^1$ to $R^3$ and $R^5$ and $R^4$ and $R^5$ together have the above-stated meaning, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

Substituted 5-aminomethyl-1H-pyrrole-2-carboxylic acid amides according to the invention of formula I are further preferred, in which $R^5$ denotes a linear or branched, saturated or unsaturated, unsubstituted aliphatic $C_{1-10}$ residue, a saturated or unsaturated, unsubstituted or at least monosubstituted 3-, 4-, 5-, 6-, 7-, 8- or 9-membered cycloaliphatic residue optionally comprising at least one heteroatom as a ring member, which cycloaliphatic residue may be attached via a linear or branched $C_{1-3}$-alkylene group, or denotes an unsubstituted or at least monosubstituted 5- to 14-membered aryl or heteroaryl residue attached via a linear or branched $C_{1-3}$ alkylene group.

$R^5$ preferably denotes a linear or branched, unsubstituted $C_{1-5}$ alkyl residue, an unsaturated or saturated, unsubstituted or at least monosubstituted 3-, 4-, 5-, 6-, 7-, 8- or 9-membered cycloaliphatic residue, or denotes an unsubstituted or at least monosubstituted phenyl residue attached via a linear or branched $C_{1-3}$ alkylene group.

$R^5$ particularly preferably denotes an alkyl residue selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl residue or denotes an unsubstituted or at least monosubstituted benzyl residue, and in each case the residues $R^1$ to $R^4$ and $R^4$ and $R^5$ together have the above-stated meaning, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

Likewise preferred substituted 5-aminomethyl-1H-pyrrole-2-carboxylic acid amides according to the invention of formula I are those in which $R^4$ and $R^5$, together with the nitrogen atom joining them together as a ring member, form a saturated or unsaturated, unsubstituted or at least monosubstituted 4-, 5-, 6-, 7-, 8- or 9-membered cycloaliphatic residue optionally comprising at least one further heteroatom as a ring member.

Preferably $R^4$ and $R^5$ together with the nitrogen atom joining them as a ring member form a saturated or unsaturated 4-, 5-, 6-, 7-, 8- or 9-membered cycloaliphatic residue optionally comprising at least one further heteroatom selected from the group consisting of nitrogen, oxygen and sulfur as a ring member, which cycloaliphatic residue may be identically or differently mono- or polysubstituted with a substituent selected from the group consisting of $C_{1-5}$ alkyl, —C(=O)—O—$C_{1-5}$-alkyl, —O—$C_{1-5}$-alkyl, Cl, F, Br, I, —C(=O)—NH$_2$, —C(=O)—NH—$C_{1-5}$-alkyl, —C(=O)—N($C_{1-5}$-alkyl)$_2$, —C(=O)—$C_{1-5}$-alkyl, —NH$_2$, —NH—$C_{1-5}$-alkyl, —N($C_{1-5}$-alkyl)$_2$, furanyl, thiophenyl, pyridinyl, phenyl and benzyl, wherein the cyclic substituents may themselves be unsubstituted or at least monosubstituted, Particularly preferably $R^4$ and $R^5$ together with the nitrogen atom joining them as a ring member form an imidazolidinyl, aziridinyl, azetidinyl, pyrrolidinyl, piperidinyl, azepanyl, azocanyl, piperazinyl, morpholinyl or thiomorpholinyl residue, which may be identically or differently mono- or polysubstituted with a substituent selected from the group consisting of $C_{1-5}$ alkyl, —C(=O)—O—$C_{1-5}$-alkyl, —O—$C_{1-5}$-alkyl, Cl, F, Br, I, —C(=O)—NH$_2$, —C(=O)—NH—$C_{1-5}$-alkyl, —C(=O)—N($C_{1-5}$-alkyl)$_2$, —C(=O)—$C_{1-5}$-alkyl, —NH$_2$, —NH—$C_{1-5}$-alkyl, —N($C_{1-5}$-alkyl)$_2$, furanyl, thiophenyl, pyridinyl, phenyl and benzyl, wherein the cyclic substituents may themselves be unsubstituted or at least monosubstituted, and in each case the residues $R^1$ to $R^3$ and $R^4$ and $R^5$ mutually independently have the above-stated meaning, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

If $R^3$ denotes a linear or branched, saturated or unsaturated aliphatic residue, i.e. a linear or branched alkyl, alkenyl or alkynyl residue, which is mono- or polysubstituted, for example mono-, di-, tri-, tetra- or pentasubstituted, the substituents thereof may mutually independently preferably be selected from the group consisting of halogen, hydroxy, —CN, —CF$_3$, —CHF$_2$, —CH$_2$F, $C_{1-5}$ alkoxy, —NH$_2$, —NH—$C_{1-5}$-alkyl, —N($C_{1-5}$-alkyl)$_2$ and optionally at least monosubstituted phenyl, particularly preferably from the group consisting of F, Cl, Br and hydroxy. If the phenyl substituent is itself mono- or polysubstituted, for example mono-, di-, tri-, tetra- or pentasubstituted, the substituents thereof may mutually independently preferably be selected from the group consisting of hydroxy, F, Cl, Br, I, —NH$_2$, —NH—$C_{1-5}$-alkyl, —N($C_{1-5}$-alkyl)$_2$, —C(=O)—NH$_2$, —C(=O)—NH—$C_{1-5}$-alkyl, —C(=O)—N($C_{1-5}$-alkyl)$_2$, —NO$_2$, —CN, —CF$_3$, —CHF$_2$, —CH$_2$F, $C_{1-5}$ alkyl and $C_{1-5}$ alkoxy.

Examples of suitable alkyl, alkenyl and alkynyl residues, which may be mono- or polysubstituted, for example mono-, di-, tri-, tetra- or pentasubstituted, include methyl, ethyl, n-propyl, iso-propyl, n-butyl, iso-butyl, sec-butyl, tert-butyl, n-pentyl, iso-pentyl, neopentyl, n-hexyl, 1-hexyl, n-heptyl, n-octyl, n-nonyl, n-decyl, —C(H)(C$_2$H$_5$)$_2$, —C(H)(n-C$_3$H$_7$)$_2$, —CH$_2$—CH$_2$—C(H)(CH$_3$)—(CH$_2$)$_3$—CH$_3$, vinyl, ethynyl, propenyl, allyl, propynyl, butenyl, butynyl, pentenyl, pentynyl, hexenyl, and hexynyl.

The monocyclic cycloaliphatic residue optionally comprising at least one further heteroatom as a ring member formed by $R^1$ and $R^2$, together with the nitrogen atom joining them together as a ring member, is saturated or unsaturated, but not aromatic. It may be identically or differently, mono- or polysubstituted, for example mono-, di-, tri-, tetra- or pentasubstituted, wherein the substituents may mutually independently preferably be selected from the group consisting of $C_{1-5}$ alkyl, —C(=O)—O—$C_{1-5}$-alkyl, —O—$C_{1-5}$-alkyl, Cl, F, Br, I, —C(=O)—NH$_2$, —C(=O)—NH—$C_{1-5}$-alkyl, —C(=O)—N($C_{1-5}$-alkyl)$_2$, —C(=O)—$C_{1-5}$-alkyl, —NH$_2$, —NH—$C_{1-5}$-alkyl, —N($C_{1-5}$-alkyl)$_2$, furanyl, thiophenyl, phenyl, pyridinyl and benzyl, particularly preferably from the group consisting of methyl, ethyl, n-propyl, iso-propyl, —C(=O)—O—CH$_3$, —C(=O)—O—C$_2$H$_5$, —C(=O)—O—(n-C$_3$H$_7$), —C(=O)—O—(iso-C$_3$H$_7$) and optionally phenyl attached via a —(CH$_2$) group. The respective furanyl, thiophenyl, pyridinyl, phenyl or benzyl substituent itself be mono- or polysubstituted, optionally mono-, di-, tri-, tetra- or pentasubstituted, in the ring system, wherein the substituents thereof may mutually independently preferably be selected from the group consisting of hydroxy, F, Cl, Br, I, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, —NO$_2$, —CN, —CF$_3$, —CHF$_2$, —CH$_2$F, C$_{1-5}$ alkyl and C$_{1-5}$ alkoxy.

If the residues R$^4$ and R$^5$, together with the nitrogen atom joining them together as a ring member, form a cycloaliphatic residue optionally comprising at least one further heteroatom as a ring member, this monocyclic residue may be saturated or unsaturated but not aromatic. It may be identically or differently, mono- or polysubstituted, for example mono-, di-, tri-, tetra- or pentasubstituted, wherein the substituents may mutually independently preferably be selected from the group consisting of C$_{1-5}$ alkyl, —C(=O)—O—C$_{1-5}$-alkyl, —O—C$_{1-5}$-alkyl, Cl, F, Br, I, —C(=O)—NH$_2$, —C(=O)—NH—C$_{1-5}$-alkyl, —C(=O)—N(C$_{1-5}$-alkyl)$_2$, —C(=O)—C$_{1-5}$-alkyl, —NH$_2$, —NH—C$_{1-5}$-alkyl, —N(C$_{1-5}$-alkyl)$_2$, furanyl, thiophenyl, pyridinyl, phenyl and benzyl, particularly preferably from the group consisting of methyl, ethyl, n-propyl, iso-propyl, —C(=O)—O—CH$_3$, —C(=O)—O—C$_2$H$_5$, —C(=O)—O—(n-C$_3$H$_7$), —C(=O)—O—(iso-C$_3$H$_7$) and phenyl optionally attached via a —(CH$_2$) group. The respective furanyl, thiophenyl, pyridinyl, phenyl or benzyl substituent itself be mono- or polysubstituted, optionally mono-, di-, tri-, tetra- or pentasubstituted, wherein the substituents thereof may preferably be selected from the group consisting of hydroxy, F, Cl, Br, I, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, —NO$_2$, —CN, —CF$_3$, —CHF$_2$, —CH$_2$F, C$_{1-5}$ alkyl and C$_{1-5}$ alkoxy.

If the residues R$^1$ and R$^2$ and/or the residues R$^4$ and R$^5$, together with the nitrogen atom joining them together as a ring member, form a cycloaliphatic residue which comprises one or more, for example 1, 2 or 3, heteroatoms as ring members, the heteroatoms, unless otherwise stated, may mutually independently preferably be selected from the group consisting of oxygen, nitrogen and sulfur.

If residues R$^1$ and R$^2$ and/or residues R$^4$ and R$^5$, together with the nitrogen atom joining them together as a ring member, form a cycloaliphatic residue optionally comprising at least one further heteroatom as a ring member, which cycloaliphatic residue may be mono- or polysubstituted, for example mono-, di-, tri-, tetra- or pentasubstituted, said residue may preferably be selected from the group consisting of imidazolidinyl, aziridinyl, azetidinyl, pyrrolidinyl, piperidinyl, azepanyl, azocanyl, piperazinyl, morpholinyl and thiomorpholinyl.

If one or more of the above-stated residues R$^3$ to R$^5$ denotes a saturated or unsaturated cycloaliphatic residue, optionally comprising at least one further heteroatom as a ring member, or comprise such a residue which is identically or differently mono- or polysubstituted, optionally mono-, di-, tri-, tetra- or pentasubstituted, the corresponding substituents may mutually independently preferably be selected from the group consisting of C$_{1-5}$ alkyl, —C(=O)—O—C$_{1-5}$-alkyl, —O—C$_{1-5}$-alkyl, Cl, F, Br, I, —C(=O)—NH$_2$, —C(=O)—NH—C$_{1-5}$-alkyl, —C(=O)—N(C$_{1-5}$-alkyl)$_2$, —C(=O)—C$_{1-5}$-alkyl, —NH$_2$, —NH—C$_{1-5}$-alkyl, —N(C$_{1-5}$-alkyl)$_2$, furanyl, thiophenyl, pyridinyl, phenyl- and benzyl, particularly preferably from the group consisting of methyl, ethyl, n-propyl, iso-propyl, —C(=O)—O—CH$_3$, —C(=O)—O—C$_2$H$_5$, —C(=O)—O—(n-C$_3$H$_7$), —C(=O)—O—(iso-C$_3$H$_7$) and phenyl optionally attached via a —(CH$_2$) group. If the furanyl, thiophenyl, pyridinyl, phenyl or benzyl substituent is itself mono- or polysubstituted, optionally mono-, di-, tri-, tetra- or pentasubstituted, the substituents thereof may mutually independently preferably be selected from the group consisting of hydroxy, F, Cl, Br, I, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, —NO$_2$, —CN, —CF$_3$, —CHF$_2$, —CH$_2$F, C$_{1-5}$ alkyl and C$_{1-5}$ alkoxy. Unless otherwise stated, the heteroatoms may mutually independently preferably be selected from the group consisting of oxygen, nitrogen and sulfur. The stated cycloaliphatic residues 1 or 2 may preferably comprise further heteroatoms as ring member(s).

Examples of suitable cycloaliphatic residues, which may be mono- or polysubstituted, for example mono-, di-, tri-, tetra- or pentasubstituted, include cyclopropyl, cyclobutyl, cyclopentyl, cyclohexyl, cycloheptyl, cyclooctyl, cyclononyl, cyclopentenyl, cyclohexenyl, cycloheptenyl and cyclooctenyl.

Examples of suitable cycloaliphatic residues comprising one or more heteroatoms as a ring member, which cycloaliphatic residues may be mono- or polysubstituted, for example mono-, di-, tri-, tetra- or pentasubstituted, include imidazolidinyl, aziridinyl, azetidinyl, pyrrolidinyl, piperidinyl, azepanyl, azocanyl, piperazinyl, tetrahydrofuranyl (tetrahydrofuryl), morpholinyl and thiomorpholinyl.

If one or more of the above-stated residues R$^3$ to R$^5$ comprise a mono- or polysubstituted, for example mono-, di-, tri-, tetra- or pentasubstituted, aryl residue, the corresponding substituents may in each case mutually independently preferably be selected from the group consisting of halogen, hydroxy, —CN, —CF$_3$, —CHF$_2$, —CH$_2$F, —NO$_2$, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, C$_{1-5}$ alkyl, C$_{1-5}$ alkoxy and optionally at least monosubstituted phenyl, particularly preferably from the group consisting of F, Cl, Br, hydroxy, —OCH$_3$ and —CH$_3$. If the phenyl substituent is itself mono- or polysubstituted, for example mono-, di-, tri-, tetra- or pentasubstituted, the substituents thereof may preferably be selected from the group consisting of hydroxy, F, Cl, Br, I, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, —NO$_2$, —CN, —CF$_3$, —CHF$_2$, —CH$_2$F, C$_{1-5}$ alkyl and C$_{1-5}$ alkoxy.

Examples of suitable aryl residues, which may be mono- or polysubstituted, include phenyl, 1-naphthyl and 2-naphthyl.

If one or more of the above-stated residues R$^3$ to R$^5$ comprise a mono- or polysubstituted, for example mono-, di-, tetra- or pentasubstituted, heteroaryl residue, the corresponding substituents may in each case mutually independently preferably be selected from the group consisting of halogen, hydroxy, —CN, —CF$_3$, —CHF$_2$, —CH$_2$F, —NO$_2$, —NH$_2$, —NH—C$_{1-5}$-alkyl, —N(C$_{1-5}$-alkyl)$_2$, —C(=O)—NH$_2$, —C(=O)—NH—C$_{1-5}$-alkyl, —C(=O)—N(C$_{1-5}$-alkyl)$_2$, C$_{1-5}$ alkyl, C$_{1-5}$ alkoxy and optionally at least monosubstituted phenyl, particularly preferably from the group consisting of F, Cl, Br, hydroxy, —OCH$_3$ and —CH$_3$. If the phenyl substituent is itself mono- or polysubstituted, for example mono-, di-, tri-, tetra- or pentasubstituted, the substituents thereof may preferably be selected from the group consisting of hydroxy, F, Cl, Br, I, —NH$_2$, —NH—C$_{1-5}$-alkyl, —N(C$_{1-5}$-alkyl)$_2$, —C(=O)—NH$_2$, —C(=O)—NH—C$_{1-5}$- alkyl, —C(=O)—N($C_{1-5}$-alkyl)$_2$, —NO$_2$, —CN, —CF$_3$, —CHF$_2$, —CH$_2$F, $C_{1-5}$ alkyl and $C_{1-5}$ alkoxy. The heteroaryl residue is preferably monocyclic and contains one, two or three heteroatoms selected from the group consisting of oxygen, sulfur and nitrogen.

Examples of suitable heteroaryl residues include pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl.

The above-stated $C_{1-5}$ alkyl and $C_{1-5}$ alkoxy residues may in each case be linear or branched. The $C_{1-5}$ alkyl residues comprise the residues methyl, ethyl, n-propyl, iso-propyl, n-butyl, iso-butyl, sec-butyl, tert-butyl, n-pentyl, iso-pentyl and neopentyl, the $C_{1-5}$ alkoxy residues comprise the residues methoxy, ethoxy, n-propoxy, iso-propoxy, n-butoxy, iso-butoxy, sec-butoxy, tert-butoxy, n-pentoxy, iso-pentoxy and neopentoxy.

Very particularly preferred substituted 5-aminomethyl-1H-pyrrole-2-carboxylic acid amides according to the invention are those selected from the group consisting of:

1-methyl-5-(4-methyl-piperidin-1-ylmethyl)-1H-pyrrole-2-carboxylic acid benzylmethyl amide,
(5-azepan-1-ylmethyl-1-methyl-1H-pyrrol-2-yl)-pyrrolidin-1-yl methanone,
[1-methyl-5-(2-methyl-piperidin-1-ylmethyl)-1H-pyrrol-2-yl]-pyrrolidin-1-yl methanone,
1-methyl-5-pyrrolidin-1-ylmethyl-1H-pyrrole-2-carboxylic acid benzyl amide,
1-methyl-5-(2-methyl-piperidin-1-ylmethyl)-1H-pyrrole-2-carboxylic acid benzyl-methyl amide,
1-(5-dibenzylcarbamoyl-1-methyl-1H-pyrrol-2-ylmethyl)-piperidine-4-carboxylic acid ethyl ester,
5-(4-benzyl-piperidin-1-ylmethyl)-1-methyl-1H-pyrrole-2-carboxylic acid cyclohexylmethyl amide,
[5-(4-benzyl-piperidin-1-ylmethyl)-1-methyl-1H-pyrrol-2-yl]-piperidin-1-yl methanone,
1-methyl-5-(2-methyl-piperidin-1-ylmethyl)-1H-pyrrole-2-carboxylic acid benzylisopropyl amide and
[1-methyl-5-(2-methyl-piperidin-1-ylmethyl)-1H-pyrrol-2-yl]-piperidin-1-yl methanone, in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts or in each case in the form of corresponding solvates.

The present invention also provides a process for the production of substituted 5-aminomethyl-1H-pyrrole-2-carboxylic acid amides according to the invention of formula I in accordance with which a substituted 1H-pyrrole-2-carboxylic acid amide of formula II

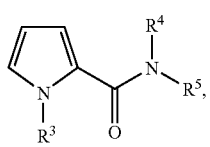

II in which the residues R$^3$, R$^4$ and R$^5$ have the above-stated meaning, is reacted using conventional methods known to the person skilled in the art, preferably in a suitable solvent, such as for example CH$_2$Cl$_2$, CH$_3$CN, dimethylformamide (DMF) or mixtures of at least two of these solvents, at room temperature (approx. 20-25° C.) with an iminium salt of formula III,

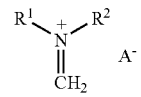

III in which R$^1$ to R$^2$ have the above-stated meaning and A$^-$ denotes a suitable anion, preferably Cl$^-$, AlCl$_4^-$, Br$^-$, I$^-$ or CF$_3$—SO$_3^-$ (triflate anion), to yield a substituted 5-aminomethyl-1H-pyrrole-2-carboxylic acid amide according to the invention of formula I and this latter compound is optionally purified using conventional methods known to the person skilled in the art, preferably by extraction, and optionally isolated.

The compounds of formula II may be produced using conventional methods known to the person skilled in the art, for example from the commercially obtainable reagents of formula IV

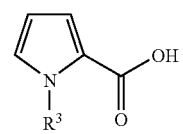

IV as described for example in A. J. Carpenter, D. J. Chadwick, Journal of Organic Chemistry, 1985, 50, pages 4362-4368 and in T. J. Donohoe, P. M. Guyo, Journal of Organic Chemistry 1996, 61, pages 7664-7665. The corresponding literature description is hereby introduced as a reference and is deemed to be part of the disclosure.

The iminium salts of formula III may likewise be obtained using conventional methods known to the person skilled in the art, for example from the corresponding aminals of formula V below

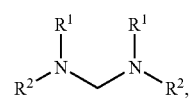

V in which residues R$^1$ and R$^2$ have the above-stated meaning, as for example described in H. Heaney, Tetrahedron 1997, 53, pages 2941-2958 and H. Heaney, Tetrahedron Lett. 1988, 29, pages 2377-2380. The corresponding literature descriptions are hereby introduced as a reference and are deemed to be part of the disclosure.

The aminals of formula V may also be produced using methods known from the literature, as for example described in H. Heaney, Tetrahedron 1997, 53, pages 2941-2958 and H. Heaney, Tetrahedron Lett. 1988, 29, pages 2377-2380, the disclosures of which are hereby incorporated by reference.

The substituted 5-aminomethyl-1H-pyrrole-2-carboxylic acid amides according to the invention of formula I and corresponding stereoisomers may be isolated not only in the form of the free bases or free acids thereof, but also in the form of corresponding salts, in particular physiologically acceptable salts.

The free bases of the respective 5-aminomethyl-1H-pyrrole-2-carboxylic acid amides according to the invention of formula I and corresponding stereoisomers may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the respective 5-aminomethyl-1H-pyrrole-2-carboxylic acid amides according to the invention of formula I and corresponding stereoisomers may preferably be converted into the corresponding hydrochlorides by combining the compounds of formula I or corresponding stereoisomers as free bases dissolved in a suitable organic solvent, such as for example butan-2-one (methyl ethyl ketone), with trimethylsilyl chloride (TMSCI).

The free bases of the respective 5-aminomethyl-1H-pyrrole-2-carboxylic acid amides of formula I and corresponding stereoisomers may likewise be converted into the corresponding physiologically acceptable salts with the free acid or a salt of a sugar substitute, such as for example saccharin, cyclamate or acesulfame.

The free acids of the respective 5-aminomethyl-1H-pyrrole-2-carboxylic acid amides of formula I and corresponding stereoisomers may accordingly be converted into the corresponding salts, in particular physiologically acceptable salts by reaction with a suitable base.

The 5-aminomethyl-1H-pyrrole-2-carboxylic acid amides according to the invention of formula I and corresponding stereoisomers may optionally, like the corresponding acids, the corresponding bases or salts of these compounds, also be obtained in the form of the solvates thereof, preferably the hydrates thereof, by conventional methods known to the person skilled in the art.

If the substituted 5-aminomethyl-1H-pyrrole-2-carboxylic acid amides according to the invention of formula I are obtained after the production thereof in the form of the stereoisomers thereof, preferably in the form of the racemates thereof or other mixtures of their various enantiomers and/or diastereomers and/or rotamers, these may be separated and optionally isolated by conventional methods known to the person skilled in the art. Examples which may be mentioned are chromatographic separation methods, in particular liquid chromatography methods at standard pressure or at elevated pressure, preferably MPLC and HPLC methods, and fractional crystallisation methods. Individual enantiomers, e.g. diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted 5-aminomethyl-1H-pyrrole-2-carboxylic acid amides according to the invention of formula I and corresponding stereoisomers as well as in each case the corresponding acids, bases, salts and solvates are toxicologically safe and are therefore suitable as pharmaceutical active ingredients in pharmaceutical preparations.

The present invention accordingly further provides pharmaceutical preparations containing at least one substituted 5-aminomethyl-1H-pyrrole-2-carboxylic acid amide according to the invention of formula I, optionally in the form of the racemate thereof, one of the pure stereoisomers thereof, in particular enantiomers or diastereomers, or in the form of mixtures of the stereoisomers, in particular the enantiomers, diastereomers and/or rotamers, in any desired mixing ratio, or in each case in the form of corresponding salts, in particular the physiologically acceptable salts, particularly preferably the hydrochlorides, or corresponding solvates, in particular the hydrates, and optionally physiologically acceptable auxiliary substances.

These pharmaceutical preparations according to the invention are in particular suitable for opioid receptor regulation, preferably for µ opioid receptor regulation, for regulating noradrenalin (NA) uptake, preferably for inhibiting noradrenalin (NA) uptake, and for regulating 5-hydroxytryptamine (5-HT) uptake, preferably for inhibiting 5-hydroxytryptamine (5-HT) uptake.

The pharmaceutical preparations according to the invention are likewise preferably suitable for the prevention and/or treatment of disorders or diseases, which are at least partially mediated by opioid receptors, in particular µ opioid receptors, and/or noradrenalin (NA) receptors and/or 5-hydroxytryptamine (5-HT) receptors.

The pharmaceutical preparations according to the invention are likewise preferably suitable for combating pain, preferably selected from the group consisting of chronic pain, acute pain and neuropathic pain, for the prevention and/or treatment of withdrawal symptoms, memory disorders, neurodegenerative diseases, preferably selected from the group consisting of Parkinson's disease, Huntington's chorea, Alzheimer's disease and multiple sclerosis, epilepsy, cardiovascular disorders, water retention conditions, intestinal motility (diarrhoea), urinary incontinence, anorexia, tinnitus, pruritus, depression, sexual dysfunction, preferably erectile dysfunction or airways diseases, for the prevention and/or treatment of disorders of food intake, preferably selected from the group consisting of obesity, bulimia, anorexia, cachexia and type II diabetes (non-insulin-dependent diabetes), or for anxiolysis, for diuresis, for suppressing the urinary reflex, for reducing the addictive potential of opioids, preferably morphine, for modulating locomotor activity, for influencing the cardiovascular system, preferably for vasodilating the arteries, or for regulating the electrolyte balance.

The pharmaceutical preparations according to the invention are particularly preferably suitable for the treatment of pain, preferably selected from the group consisting of chronic pain, acute pain and neuropathic pain.

The present invention also provides the use one or more substituted 5-aminomethyl-1H-pyrrole-2-carboxylic acid amides of formula I in each case optionally in the form of the pure stereoisomers thereof, in particular enantiomers or diastereomers, the racemates thereof or in the form of mixtures of the stereoisomers, in particular the enantiomers, diastereomers and/or rotamers, in any desired mixing ratio, or in each case in the form of corresponding salts, in particular the physiologically acceptable salts, particularly preferably the hydrochlorides, or in each case in the form of corresponding solvates, in particular the hydrates, for the production of a pharmaceutical preparation for opioid receptor regulation, preferably for µ opioid receptor regulation, for regulating noradrenalin (NA) uptake, preferably for inhibiting noradrenalin (NA) uptake or for regulating hydroxytryptamine (5-HT) uptake, preferably for inhibiting 5-hydroxytryptamine (5-HT) uptake.

The present invention also provides the use of one or more substituted 5-aminomethyl-1H-pyrrole-2-carboxylic acid amides of formula I, optionally in the form of the pure stereoisomers thereof, in particular enantiomers or diastereomers, the racemates thereof or in the form of mixtures of the stereoisomers, in particular the enantiomers, diastereomers and/or rotamers in any desired mixing ratio, or in each case in the form of corresponding salts, in particular the physiologically acceptable salts, particularly preferably the hydrochlorides, or in each case in the form of corresponding solvates, in particular the hydrates, for the production of a pharmaceutical preparation for combating pain, preferably selected from the group consisting of chronic pain, acute pain and neuropathic pain, for the prevention and/or treatment of withdrawal symptoms, memory disorders, neurodegenerative diseases, preferably selected from the group consisting of Parkinson's disease, Huntington's chorea, Alzheimer's disease and/or multiple sclerosis, epilepsy, cardiovascular disorders, water retention conditions, intestinal motility (diarrhoea), urinary incontinence, anorexia, tinnitus, pruritus, depression, sexual dysfunction, preferably erectile dysfunction, or airways diseases, for the prevention and/or treatment of disorders of food intake, preferably selected from the group consisting of obesity, bulimia, anorexia, cachexia and type II diabetes (non-insulin-dependent diabetes), or for anxiolysis, for diuresis, for suppressing the urinary reflex, for reducing the addictive potential of opioids, preferably morphine, for modulating locomotor activity, for influencing the cardiovascular system, preferably for vasodilating the arteries, or for regulating the electrolyte balance.

The pharmaceutical preparations according to the invention may assume the form of liquid, semisolid or solid dosage forms, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally press-moulded into tablets, packaged in capsules or suspended in a liquid, and also be administered as such.

In addition to one or more substituted 5-aminomethyl-1H-pyrrole-2-carboxylic acid amides of formula I, in each case optionally in the form of the racemates thereof, the pure stereoisomers thereof, in particular enantiomers or diastereomers, or in the form of mixtures of the stereoisomers, in particular the enantiomers, diastereomers and/or rotamers, in any desired mixing ratio, or in each case in the form of a corresponding salt, in particular a physiologically acceptable salt, or in the form of a corresponding solvate, in particular of the hydrate, the pharmaceutical preparations according to the invention conventionally contain further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes and eyes.

Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

Substituted 5-aminomethyl-1H-pyrrole-2-carboxylic acid amides of formula I, optionally in the form of the racemates thereof, the pure stereoisomers thereof, in particular enantiomers or diastereomers, or in the form of mixtures of the stereoisomers, in particular the enantiomers, diastereomers and/or rotamers, in any desired mixing ratio, or in each case in the form of a corresponding salt, in particular a physiologically acceptable salt, or in the form of a corresponding solvate, in particular the hydrate, in a depot in dissolved form or in a dressing, optionally with the addition of skin penetration promoters, are suitable percutaneous administration preparations.

Orally or percutaneously administrable formulations may also release the particular substituted 5-aminomethyl-1H-pyrrole-2-carboxylic acid amides of formula I optionally in the form of the racemates thereof, the pure stereoisomers thereof, in particular the enantiomers or diastereomers, or in the form of mixtures of the stereoisomers, in particular of the enantiomers, diastereomers and/or rotamers, in any desired mixing ratio, or in each case in the form of a corresponding salt, in particular of a physiologically acceptable salt, or in the form of a corresponding solvate, in particular the hydrate, in delayed manner Production of the pharmaceutical preparations according to the invention proceeds with the assistance of conventional means, devices, methods and processes known to the person skilled in the art, such as are described for example in A. R. Gennaro (ed.), "Remington's Pharmaceutical Sciences", 17th edition, Mack Publishing Company, Easton, Pa. (1985), in particular in part 8, chapters 76 to 93, the disclosure of which is hereby incorporated by reference.

The quantity to be administered to the patient of the particular substituted 5-aminomethyl-1H-pyrrole-2-carboxylic acid amide of formula I, optionally in the form of the racemate thereof, the pure stereoisomer thereof, in particular enantiomer or diastereomer, or in the form of mixtures of the stereoisomers, in particular the enantiomers, diastereomers and/or rotamers, in any desired mixing ratio or in each case in the form of a corresponding salt, in particular a physiologically acceptable salt, or in each case of a corresponding solvate thereof, in particular the hydrate, may vary and is for example dependent on the weight or age of the patient and on the mode of administration, the indication and the severity of the complaint. Conventionally, 0.005 to 500 mg/kg, preferably 0.05 to 50 mg/kg of patient body weight of at least one substituted 5-aminomethyl-1H-pyrrole-2-carboxylic acid amide of formula, optionally in the form of the racemate thereof, the pure stereoisomers thereof, in particular enantiomers or diastereomers, or in the form of mixtures of the stereoisomers, in particular the enantiomers or diastereomers, in any desired mixing ratio, or in each case in the form of a corresponding salt, in particular a physiologically acceptable salt, or in the form of a corresponding solvate, in particular the hydrate, are administered.

PHARMACOLOGICAL METHODS a) Method for Determining Affinity for Human μ Opioid Receptor Receptor affinity for the human μ opioid receptor is determined in a homogeneous batch in microtitre plates. To this end, dilution series of the particular substituted 5-aminomethyl-1H-pyrrole-2-carboxylic acid amide of formula I to be tested are incubated at room temperature for 90 minutes in a total volume of 250 μl with a receptor membrane preparation (15-40 μg of protein per 250 μl of incubation batch) of CHO-K1 cells, which express the human μ opioid receptor (μ opiate receptor) (RB-HOM receptor membrane preparation from NEN, Zaventem, Belgium) in the presence of 1 nmol/l of the radioactive ligand [$^3$H]-naloxone (NET719, from NEN, Zaventem, Belgium) and of 1 mg of WGA-SPA beads (wheat germ agglutinin SPA beads from Amersham/Pharmacia, Freiburg, Germany). The incubation buffer used is 50 mmol/l tris-HCl supplemented with 0.05 wt. % of sodium azide and with 0.06 wt. % of bovine serum albumin. 25 µmol/l of naloxone were additionally added to determine nonspecific binding. Once the ninety minute incubation time had elapsed, the microtitre plates were centrifuged off for 20 minutes at 1000 g and the radioactivity measured in a β-Counter (Microbeta-Trilux, from PerkinElmer Wallac, Freiburg, Germany). The percentage displacement of the radioactive ligand from its binding to the human µ opiate receptor is determined at a concentration of the compounds to be tested of 1 µmol/l and stated as percentage inhibition of specific binding. On the basis of the percentage displacement by different concentrations of the compounds to be tested of formula I, $IC_{50}$ inhibition concentrations which bring about 50% displacement of the radioactive ligand were calculated. $K_i$ values for the test substances may be obtained by conversion using the Cheng-Prusoff equation.

b) Method for Determining Noradrenalin and 5-HT Uptake Inhibition:

Synaptosomes from rat brain regions are freshly isolated for in vitro studies, as described in the publication "The isolation of nerve endings from brain" by E. G. Gray and V. P. Whittaker, J. Anatomy 96, pages 79-88, 1962, the disclosure of which is hereby incorporated by reference. The tissue (hypothalamus for the determination of noradrenalin uptake inhibition and medulla and pons for the determination of 5-HT uptake inhibition) is homogenized in ice-cooled 0.32 M sucrose (100 mg of tissue/1 ml) in a glass homogenizer with Teflon pestle using five complete up and down strokes at 840 revolutions/minute. The homogenate is centrifuged at 4° C. for 10 minutes at 1000 g. After subsequent centrifugation at 17000 g for 55 minutes, the synaptosomes ($P_2$ fraction) are obtained, which are resuspended in 0.32 M glucose (0.5 ml/100 mg of original weight).

The particular uptake is measured in a 96-well microtitre plate. The volume is 250 µl and the incubation proceeds at room temperature (approx. 20-25° C.) under an $O_2$ atmosphere. The incubation time is 7.5 minutes for [$^3$H]-NA and 5 minutes for [$^3$H]-5-HT. The 96 samples are then filtered through a Unifilter GF/B® microtitre plate (Packard) and washed with 200 ml of incubated buffer using a "Brabdel MPXRI-96T Cell-Harvester". The Unifilter GF/B plate is dried for 1 hour at 55° C. The plate is then sealed with a Back Seal® (Packard) and 35 µl of scintillation fluid are added per well (Ultima Gold®, Packard). After sealing with a Top Seal® (Packard) and establishing an equilibrium (around 5 hours), radioactivity is determined in a "Trilux 1450 Microbeta" (Wallac).

The quantity of protein used in the above determination corresponds to the values known from the literature, as for example described in "Protein measurement with the folin phenol reagent", Lowry et al., J. Biol. Chem., 193, 265-275, 1951. A detailed description of the method may additionally be found in the literature, for example in M. Ch. Frink, H.-H. Hennies, W. Engelberger, M. Haurand and B. Wilffert (1996) Arzneim.-Forsch./Drug Res. 46 (III), 11, 1029-1036, the disclosures of which are hereby incorporated by reference.

The following characteristics were determined for the NA or 5-HT transporter:

NA uptake: Km=0.32±0.11 µM

5HT uptake: Km=0.084±0.011 µM.

c) Investigation of Analgesic Efficacy by the Writhing Test

Investigation of the compounds according to the invention of formula I for analgesic efficacy is performed by phenylquinone-induced writhing in the mouse, modified after I. C. Hendershot and J. Forsaith (1959) J. Pharmacol. Exp. There. 125, 237-240. The corresponding literature description is hereby introduced as a reference and is deemed to be part of the disclosure.

Male NMRI mice weighing from 25 to 30 g were used for this purpose. Groups of 10 animals per compound dose receive, 10 minutes after intravenous administration of the compounds to be tested, 0.3 ml/mouse of a 0.02% aqueous solution of phenylquinone (phenylbenzoquinone, Sigma, Deisenhofen, Germany; solution prepared with addition of 5% of ethanol and stored in a water bath at 45° C.) administered intraperitoneally. The animals are placed individually in observation cages. A push button counter is used to record the number of pain-induced stretching movements (writhing reactions=straightening of the torso with stretching of the rear extremities) for 5-20 minutes after phenylquinone administration. The control was provided by animals which had received only physiological common salt solution. All the compounds were tested at the standard dosage of 10 mg/kg.

EXAMPLES

The invention is explained in further detail below with reference to examples which are set forth merely as illustrations of the invention and are not intended to be limiting.

The NMR spectra were measured on a Bruker DPX 300 instrument for the 300 MHz spectra and on a Bruker DRX 600 instrument for the 600 MHz spectra. The particular chemicals and solvents used were purchased from the commercial sources.

A) General Synthesis Method for the Production of Compounds of Formula II

The particular 1H-methyl-pyrrole-2-carboxylic acid (50 mmol) of formula IV (in which $R^3$ in each case denotes a methyl group) was suspended in 200 ml of toluene. Then, with cooling in an ice bath, 100 mmol of sodium hydride (NaH) were slowly added and the mixture stirred for approx. 10 minutes at room temperature. After addition of 200 mmol of oxalyl chloride, the reaction mixture was refluxed for 15 minutes and then the excess oxalyl chloride and the reaction medium were removed in a rotary evaporator.

The resultant residue was redissolved in 200 ml of diethyl ether, slowly combined with 100 mmol of the corresponding amine of formula $NHR^4R^5$ and the resultant reaction mixture was refluxed for two hours. After cooling, the reaction mixture was washed three times with 50 ml portions of water. The organic phase was separated, dried with magnesium sulfate and evaporated in a rotary evaporator. The resultant crude product was used without further purification in the following synthesis steps.

The compounds of formula II produced by the above general synthesis method are listed in the following Table 1.

| [1] | $R^4$ | $R^5$ | $R^3$ | Yield [%] |
|---|---|---|---|---|
| II-1 | $CH_2$-phenyl | $CH_2$-phenyl | $CH_3$ | 90 |
| II-2 | ]—$(CH_2)_5$—[ | | $CH_3$ | 82 |
| II-3 | ]—$(CH_2)_4$—[ | | $CH_3$ | 74 |
| II-4 | $CH_2$-phenyl | $CH_3$ | $CH_3$ | 93 |
| II-5 | $CH_2$-phenyl | $CH(CH_3)_2$ | $CH_3$ | 93 |
| II-6 | cyclohexyl | $CH_3$ | $CH_3$ | 89 |

[1]: Compound of formula II
The structure of compounds II-1 to II-6 was in each case determined by $^1$H-NMR spectroscopy. The chemical shifts of selected compounds are shown below.

II-1 1-Methyl-1H-pyrrole-2-carboxylic acid dibenzyl amide

δ(DMSO, 300 MHz)=3.73 (s, 3H, NCH$_3$); 4.58-4.72 (m, 4H, CH$_2$Ph); 5.95 (dd 1H, J=2.6 Hz, J=6.0 Hz, N(CH$_3$—)]—CHCHCHC-[); 6.23-6.29 (m, 1H, N(CH$_3$)—]—CHCH-CHC-[); 6.88-6.93 (m, 1H, N(CH$_3$)—]—CHCHCHC-[); 7.16-7.42 (m, 10H, Ph).

II-2 (1-Methyl-1H-pyrrol-2-yl)-piperidin-1-yl methanone

δ(DMSO, 300 MHz)=1.45-1.68 (m, 6H, N—[(CH$_2$)$_2$—CH$_2$—(CH$_2$)$_2$—]); 3.51-3.62 (m, 4H, N—[(CH$_2$)$_2$—CH$_2$—(CH$_2$)$_2$—]); 3.65 (s, 3H, NCH$_3$); 5.97-6.03 (m, 1H, N(CH$_3$)—[—CHCHCHC-[); 6.21-6.25 (m, 1H, N(CH$_3$)]—CHCHCHC-[); 6.79-6.84 (m, 1H, N(CH$_3$)]—CHCHCHC-[).

II-4 1-Methyl-1H-pyrrole-2-carboxylic acid benzylmethyl amide

δ(DMSO, 300 MHz)=2.99 (br. s, 3H, NCH$_3$Bn); 3.71 (s, 3H, NCH$_3$); 4.65-4.75 (m, 2H, CH$_2$Ph); 5.96-6.04 (m, 1H, N(CH$_3$)]—CHCHCHC-[); 6.28-6.41 (m, 1H, N(CH$_3$)—]—CHCHCHC-[); 6.87-6.93 (m, 1H, N(CH$_3$)—]—CHCH-CHC-[); 7.18-7.43 (m, 5H, Ph).

II-5 1-Methyl-1H-pyrrole-2-carboxylic acid benzylisopropyl amide

δ(DMSO, 300 MHz)=1.15 (d, 3H, J=6.8 Hz, CH(CH$_3$)$_2$); 3.67 (s, 3H, NCH$_3$); 4.52-4.67 (m, 3H, CH$_2$Ph, CH(CH$_3$)$_2$); 5.95-6.03 (m, 1H, N(CH$_3$)]—CHCHCHC-[); 6.25-6.34 (m, 1H, N(CH$_3$)—]—CHCHCHC-[); 6.80-6.86 (m, 1H, N(CH$_3$)—]—CHCHCHC-[); 7.15-7.36 (m, 5H, Ph).

II-6 1-Methyl-1H-pyrrole-2-carboxylic acid cyclohexylmethyl amide

δ(DMSO, 300 MHz)=0.88-1.36 (m, 4H, N]—CH(CH$_2$)$_2$(CH$_2$)$_2$CH$_2$—[); 1.4-1.85 (m, 6H, N]—CH(CH$_2$)$_2$(CH$_2$)$_2$CH$_2$—[); 2.88 (s, 3H, N—CH$_3$); 3.64 (s, 3H, NCH$_3$); 4.03-4.19 (m, 1H, N]—CH(CH$_2$)$_2$(CH$_2$)$_2$CH$_2$—[); 5.97-6.04 (m, 1H, N(CH$_3$)]—CHCHCHC-[); 6.19-6.29 (m, 1H, N(CH$_3$)]—CHCHCHC-[); 6.79-6.85 (m, 1H, N(CH$_3$)]—CHCHCHC-[).

B) General procedure for the automated synthesis of the compounds according to the invention of formula I. Synthesis was performed in an automated synthesizer from Zymark.

Batch Quantities:
 300 μmol of aminal of formula V
 300 μmol of pyrrole of formula II
 600 μmol of acetyl chloride Pipetting Volume:
 1 ml of aminal solution
 1 ml of pyrrole solution
 0.6 ml of acetyl chloride solution Stock Solutions:
 0.3 M aminal solution in CH$_3$CN (solution I)
 0.3 M pyrrole solution in CH$_3$CN (solution II)
 1 M acetyl chloride solution in CH$_3$CN (solution III)

Synthesis Procedure:
 300 μmol of aminal compound of formula V (solution I, 1 ml) were initially introduced at 20° C. into a dry, threaded glass vial with a septum cap and combined with 600 μmol of acetyl chloride (solution III, 0.6 ml). After 1 hour, 300 μmol of pyrrole derivative of formula II (solution II, 1 ml) were added by pipette. The reaction solution was stirred for 24 hours at 20° C. 2 ml of HCl solution (0.1 M) and 2 ml of CH$_2$Cl$_2$ were then added at the quench station. The resultant solution was intermixed for 30 minutes in the spin reactor. The magnetic stir bar was removed and the vessel rinsed out with 2 ml of CH$_2$Cl$_2$.

Synthesis Work-Up:
 The lower, organic phase was removed and discarded. 4 ml of CH$_2$Cl$_2$ were added in a vortexer and then intermixed for a further 10 minutes in the spin reactor. After centrifugation, the organic phase was again removed and discarded, the aqueous phase was combined once more with 4 ml of CH$_2$Cl$_2$ and adjusted to pH 8-9 with 0.7 ml of 7.5% strength NaHCO$_3$ solution. The solution was vigorously intermixed in the spin reactor, and, after centrifugation, the organic phase was separated and collected. The aqueous phase was extracted once more in a similar manner with 4 ml of CH$_2$Cl$_2$. The combined organic phases were then dried over an MgSO$_4$ cartridge and evaporated under reduced pressure. Further purification of the compounds proceeded by preparative HPLC.

The following example compounds according to the invention of formula I were produced in this manner:

Example 1

1-Methyl-5-(4-methyl-piperidin-1-ylmethyl)-1H-pyrrole-2-carboxylic acid benzyl-methyl amide MS: (ESI) m/z=339 [M$^+$+1]; 241.

Example 2

(5-Azepan-1-ylmethyl-1-methyl-1H-pyrrol-2-yl)-pyrrolidin-1-yl methanone

MS: (ESI) m/z=290 [M$^+$+1]; 219; 191

Example 3

[1-Methyl-5-(2-methyl-piperidin-1-ylmethyl)-1H-pyrrol-2-yl]-pyrrolidin-1-yl methanone MS: (ESI) m/z=290 [M$^+$+1]; 191.

Example 4

1-Methyl-5-pyrrolidin-1-ylmethyl-1H-pyrrole-2-carboxylic acid benzyl amide

MS: (ESI) m/z=312 [M$^+$+1]; 241.

Example 5

1-Methyl-5-(2-methyl-piperidin-1-ylmethyl)-1H-pyrrole-2-carboxylic acid benzyl-methyl amide MS: (ESI) m/z=340 [M$^+$+1]; 241.

Example 6

1-(5-Dibenzylcarbamoyl-1-methyl-1H-pyrrol-2-ylmethyl)-piperidine-4-carboxylic acid ethyl ester MS: (ESI) m/z=475 [M$^+$+1]; 317; 198.

Example 7

5-(4-Benzyl-piperidin-1-ylmethyl)-1-methyl-1H-pyrrole-2-carboxylic acid cyclohexyl-methyl amide MS: (ESI) m/z=409 [M$^+$+1]; 233.

Example 8

[5-(4-Benzyl-piperidin-1-ylmethyl)-1-methyl-1H-pyrrol-2-yl]-piperidin-1-yl methanone MS: (ESI) m/z=381 [$M^+$+1]; 205.

Example 9

1-Methyl-5-(2-methyl-piperidin-1-ylmethyl)-1H-pyrrole-2-carboxylic acid benzyl-isopropyl amide MS: (ESI) m/z=368 [$M^+$+1]; 269.

Example 10

[1-Methyl-5-(2-methyl-piperidin-1-ylmethyl)-1H-pyrrol-2-yl]-piperidin-1-yl methanone MS: (ESI) m/z=304 [$M^+$+1]; 205.

Pharmacological Investigations:

a) Affinity for the μ Receptor

The affinity of the 5-aminomethyl-1H-pyrrole-2-carboxylic acid amides according to the invention for the μ receptor was determined as described above. The values for some selected compounds are shown in Table 1 below.

TABLE 1

| Compound according to Example | $R^1$, $R^2$ | $R^4$, $R^5$ | $R^3$ | OR μ1 human naloxone inhibition [%] |
|---|---|---|---|---|
| 3 | ]—(CH$_2$)$_5$-[-2-CH$_3$ | ]—(CH$_2$)$_4$—[ | CH$_3$ | 83 |
| 10 | ]—(CH$_2$)$_5$-[-2-CH$_3$ | ]—(CH$_2$)$_5$—[ | CH$_3$ | 86 | b) 5-HT Uptake Inhibition and Noradrenalin (NA) Uptake Inhibition

The 5-HT reuptake inhibition and noradrenalin reuptake inhibition of the 5-aminomethyl-1H-pyrrole-2-carboxylic acid amides according to the invention were determined as described above. The values for some selected compounds are shown in the following Table 2.

TABLE 2

| Compound according to Example | $R^1$, $R^2$ | $R^4$ | $R^5$ | $R^3$ | 5HT uptake inhibition [2] | NA uptake inhibition [3] |
|---|---|---|---|---|---|---|
| 1 | ]—(CH$_2$)$_5$-[-4-CH$_3$ | CH$_3$ | CH$_2$-phenyl | CH$_3$ | 70 | 81 |
| 2 | ]—(CH$_2$)$_6$—[ | ]—(CH$_2$)$_4$—[ | | CH$_3$ | 60 | |
| 3 | ]—(CH$_2$)$_5$-[-2-CH$_3$ | ]—(CH$_2$)$_4$—[ | | CH$_3$ | 52 | |
| 4 | ]—(CH$_2$)$_4$—[ | CH$_3$ | CH$_2$-phenyl | CH$_3$ | | 82 |
| 5 | ]—(CH$_2$)$_5$-[-2-CH$_3$ | CH$_3$ | CH$_2$-phenyl | CH$_3$ | | 81 |
| 6 | ]—(CH$_2$)$_5$-[-4-CO$_2$CH$_2$CH$_3$ | CH$_2$-phenyl | CH$_2$-phenyl | CH$_3$ | | 74 |
| 7 | ]—(CH$_2$)$_5$-[-4-CH$_2$phenyl | CH$_3$ | cyclohexyl | CH$_3$ | | 62 |
| 8 | ]—(CH$_2$)$_5$-[-4-CH$_2$phenyl | ]—(CH$_2$)$_5$—[ | | CH$_3$ | | 61 |
| 9 | ]—(CH$_2$)$_5$-[-2-CH$_3$ | CH$_2$-phenyl | CH(CH$_3$)$_2$ | CH$_3$ | | 59 |

[2] 5-HT uptake, rat, 10 μM, % inhibition
[3] NA uptake, rat, 10 μM, % inhibition The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A 5-aminomethyl-1H-pyrrole-2-carboxylic acid amide compound corresponding to formula

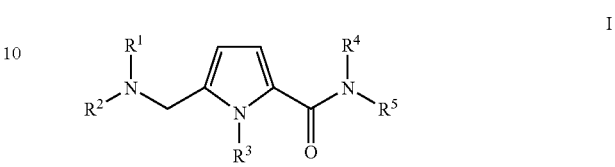

I wherein
$R^1$ and $R^2$, together with the nitrogen atom to which they are attached form a saturated, unsubstituted or at least monosubstituted cyclic group selected from the group consisting of aziridinyl, azetidinyl, pyrrolidinyl, piperidinyl, and azepanyl groups;
$R^3$ denotes a linear or branched, unsubstituted $C_{1-5}$-alkyl group;
$R^4$ denotes, a linear or branched, unsubstituted $C_{1-5}$-alkyl group; an unsubstituted or at least monosubstituted cyclic group selected from the group consisting of cyclopropyl, cyclobutyl, cyclopentyl, cyclohexyl, cycloheptyl, and cyclooctyl, which cyclic group optionally may be attached via a linear or branched $C_{1-3}$ alkylene group; or denotes an unsubstituted or at least monosubstituted phenyl group attached via a linear or branched $C_{1-3}$ alkylene group;
$R^5$ denotes a linear or branched, unsubstituted $C_{1-5}$-alkyl group; an unsubstituted or at least monosubstituted cyclic group selected from the group consisting of cyclopropyl, cyclobutyl, cyclopentyl, cyclohexyl, cycloheptyl, and cyclooctyl, which cyclic group optionally may be attached via a linear or branched $C_{1-3}$ alkylene group;

or denotes an unsubstituted or at least monosubstituted phenyl group attached via a linear or branched $C_{1-3}$ alkylene group; or $R^4$ and $R^5$, together with the nitrogen atom to which they are attached form a saturated, unsubstituted or at least monosubstituted cyclic group selected from the group consisting of aziridinyl, azetidinyl, pyrrolidinyl, piperidinyl and azepanyl;

wherein substituents of said cyclic groups are independently selected from the group consisting of $C_{1-5}$ alkyl, —C(=O)—O—$C_{1-5}$-alkyl, and benzyl;

wherein substituents of said phenyl groups are independently selected from the group consisting of halogen, hydroxy, —CN, —CF$_3$, $C_{1-5}$ alkyl and $C_{1-5}$ alkoxy;

in the form of a pure stereoisomer or a mixture of stereoisomers in any mixing ratio;

or a salt thereof.

2. A compound according to claim 1, wherein said compound is in the form of a pure enantiomer or diastereomer.

3. A compound according to claim 1, wherein said compound is in the form of a racemic mixture.

4. A compound according to claim 1, wherein $R^1$ and $R^2$ together with the nitrogen to which they are attached form a saturated, unsubstituted or at least monosubstituted cyclic group selected from the group consisting of azetidinyl, pyrrolidinyl, piperidinyl, and azepanyl.

5. A compound according to claim 1, wherein $R^3$ denotes an alkyl group selected from the group consisting of methyl, ethyl, n-propyl, iso-propyl, n-butyl, iso-butyl, sec-butyl and tert-butyl.

6. A compound according to claim 1, wherein $R^4$ denotes a linear or branched, unsubstituted $C_{1-5}$ alkyl group, an unsubstituted or at least monosubstituted cyclic group selected from the group consisting of cyclopropyl, cyclobutyl, cyclopentyl, cyclohexyl, cycloheptyl, and cyclooctyl, or denotes an unsubstituted or at least monosubstituted phenyl group attached via a linear or branched $C_{1-3}$ alkylene group.

7. A compound according to claim 1, wherein $R^4$ denotes an alkyl group selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl group or denotes an unsubstituted or at least monosubstituted benzyl group.

8. A compound according to claim 1, wherein $R^5$ denotes a linear or branched, unsubstituted $C_{1-5}$ alkyl group, an unsubstituted or at least monosubstituted cyclic group selected from the group consisting of cyclopropyl, cyclobutyl, cyclopentyl, cyclohexyl, cycloheptyl, and cyclooctyl, or denotes an unsubstituted or at least monosubstituted phenyl group attached via a linear or branched $C_{1-3}$ alkylene group.

9. A compound according to claim 1, wherein $R^5$ denotes an alkyl group selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl group or denotes an unsubstituted or at least monosubstituted benzyl group.

10. A compound according to claim 1, wherein $R^4$ and $R^5$ together with the nitrogen atom to which they are attached form a saturated, unsubstituted or at least monosubstituted cyclic group selected from the group consisting of azetidinyl, pyrrolidinyl, piperidinyl, and azepanyl.

11. A compound according to claim 1, wherein $R^4$ and $R^5$ together with the nitrogen atom to which they are attached form an aziridinyl, azetidinyl, pyrrolidinyl, piperidinyl, or azepanyl group, which group may be identically or differently mono- or polysubstituted with a substituent selected from the group consisting of $C_{1-5}$ alkyl, —C(=O)—O—$C_{1-5}$-alkyl.

12. A compound according to claim 1, wherein:

$R^1$ and $R^2$ together with the nitrogen atom to which they are attached form a saturated cyclic group selected from the group consisting of azetidinyl, pyrrolidinyl, piperidinyl, and azepanylgroups, which may be identically or differently mono- or polysubstituted with a substituent selected from the group consisting of $C_{1-5}$ alkyl, —C(=O)—O—$C_{1-5}$-alkyl, and benzyl;

$R^3$ denotes a linear or branched, unsubstituted $C_{1-5}$ alkyl group;

$R^4$ denotes a a linear or branched, unsubstituted $C_{1-5}$ alkyl group, an unsubstituted or at least monosubstituted cyclic group selected from the group consisting of cyclopropyl, cyclobutyl, cyclopentyl, cyclohexyl, cycloheptyl, and cyclooctyl, or denotes an unsubstituted or at least monosubstituted phenyl group attached via a linear or branched $C_{1-3}$ alkylene group;

$R^5$ denotes a linear or branched, unsubstituted $C_{1-5}$ alkyl group, an unsubstituted or at least monosubstituted cyclic group selected from the group consisting of cyclopropyl, cyclobutyl, cyclopentyl, cyclohexyl, cycloheptyl, and cyclooctyl, or denotes an unsubstituted or at least monosubstituted phenyl group attached via a linear or branched $C_{1-3}$ alkylene group, or $R^4$ and $R^5$, together with the nitrogen atom to which they are attached form a saturated cyclic group selected from the group consisting of azetidinyl, pyrrolidinyl, piperidinyl, and azepanyl, which may be identically or differently mono- or polysubstituted with a substituent selected from the group consisting of $C_{1-5}$ alkyl, —C(=O)—O—$C_{1-5}$-alkyl, and benzyl.

13. A compound according to claim 1, wherein:

$R^1$ and $R^2$, together with the nitrogen atom to which they are attached form an aziridinyl, azetidinyl, pyrrolidinyl, piperidinyl, or azepanyl group, which may be substituted with a substituent selected from the group consisting of methyl, ethyl, n-propyl, iso-propyl, —C(=O)—O—CH$_3$, —C(=O)—O—C$_2$H$_5$, —C(=O)—O-(n-C$_3$H$_7$), —C(=O)—O-(iso-C$_3$H$_7$) and benzyl group;

$R^3$ denotes an alkyl group selected from the group consisting of methyl, ethyl, n-propyl, iso-propyl, n-butyl, iso-butyl, sec-butyl and tert-butyl;

$R^4$ denotes an alkyl group selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl group or denotes a benzyl group;

$R^5$ denotes an alkyl group selected from the group consisting of methyl, ethyl, n-propyl, iso-propyl, n-butyl, iso-butyl, sec-butyl and tert-butyl, a cyclopropyl, cyclobutyl, cyclopentyl, cyclohexyl, cycloheptyl or cyclooctyl group, or denotes a benzyl group, or $R^4$ and $R^5$, together with the nitrogen atom to which they are attached form an aziridinyl, azetidinyl, pyrrolidinyl, piperidinyl, or azepanyl group, which may be substituted with a substituent selected from the group consisting of methyl, ethyl, n-propyl, iso-propyl, —C(=O)—O—CH$_3$, —C(=O)—O—C$_2$H$_5$, —C(=O)—O-(n-C$_3$H$_7$), —C(=O)—O-(iso-C$_3$H$_7$) and benzyl group.

14. A compound selected from the group consisting of:
1-methyl-5-(4-methyl-piperidin-1-ylmethyl)-1H-pyrrole-2-carboxylic acid benzylmethyl amide,
(5-azepan-1-ylmethyl-1-methyl-1H-pyrrol-2-yl)-pyrrolidin-1-yl methanone,
[1-methyl-5-(2-methyl-piperidin-1-ylmethyl)-1H-pyrrol-2-yl]-pyrrolidin-1-yl methanone,
1-methyl-5-pyrrolidin-1-ylmethyl-1H-pyrrole-2-carboxylic acid benzylmethyl amide,
1-methyl-5-(2-methyl-piperidin-1-ylmethyl)-1H-pyrrole-2-carboxylic acid benzyl-methyl amide,
1-(5-dibenzylcarbamoyl-1-methyl-1H-pyrrol-2-ylmethyl)-piperidine-4-carboxylic acid ethyl ester,
5-(4-benzyl-piperidin-1-ylmethyl)-1-methyl-1H-pyrrole-2-carboxylic acid cyclohexylmethyl amide,
[5-(4-benzyl-piperidin-1-ylmethyl)-1-methyl-1H-pyrrol-2-yl]-piperidin-1-yl methanone,
1-methyl-5-(2-methyl-piperidin-1-ylmethyl)-1H-pyrrole-2-carboxylic acid benzylisopropyl amide, and
[1-methyl-5-(2-methyl-piperidin-1-ylmethyl)-1H-pyrrol-2-yl]-piperidin-1-yl methanone,
in the form of a pure stereoisomer or a mixture of stereoisomers in any mixing ratio;
or a salt thereof.

15. A process for producing a 5-aminomethyl-1H-pyrrole-2-carboxylic acid amide according to claim 1, comprising:
reacting a substituted 1H-pyrrole-2-carboxylic acid amide compound corresponding to formula II:

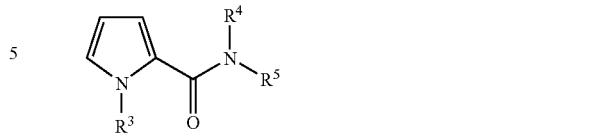

in which $R^3$, $R^4$ and $R^5$ have the meanings given in claim 1 with an iminium salt corresponding to formula III:

in which $R^1$ and $R^2$ have the meanings given in claim 1, and $A^-$ denotes a suitable anion, and
optionally isolating or purifying the resulting compound.

16. A process according to claim 15, wherein $A^-$ denotes a $Cl^-$, $AlCl_4^-$, $Br^-$, $I^-$ or $CF_3$—$SO_3^-$ anion.

17. A pharmaceutical composition comprising a compound according to claim 1 and at least one physiologically acceptable auxiliary substance.

* * * * *